United States Patent [19]

Nash

[11] 4,001,006

[45] Jan. 4, 1977

[54] DIALKYLAMMONIUM-2,4-DICHLORO-PHENOXYACETATES AS PLANT GROWTH REGULATORS AND THE METHOD OF MAKING SAME

[75] Inventor: Lawrence H. Nash, Fort Lauderdale, Fla.

[73] Assignee: Kalo Laboratories, Inc., Kansas City, Mo.

[22] Filed: June 26, 1975

[21] Appl. No.: 590,518

Related U.S. Application Data

[63] Continuation-in-part of Ser. No. 179,333, Sept. 10, 1971, abandoned, which is a continuation-in-part of Ser. No. 33,078, April 29, 1970, abandoned, which is a continuation-in-part of Ser. No. 4,087, Jan. 19, 1970, abandoned, which is a continuation-in-part of Ser. No. 700,967, Jan. 26, 1968, abandoned.

[52] U.S. Cl. .................................... 71/117; 71/66; 260/501.16
[51] Int. Cl.$^2$ ...................... A01N 9/24; C07C 53/16
[58] Field of Search ............... 260/501.16; 71/116, 71/117, 66

[56] References Cited

UNITED STATES PATENTS

2,767,071  10/1956  Morril ................................. 71/117

FOREIGN PATENTS OR APPLICATIONS

627,712  8/1949  United Kingdom ............... 71/117
851,084  10/1960  United Kingdom ............... 71/116

*Primary Examiner*—Gerald A. Schwartz
*Attorney, Agent, or Firm*—Stanley D. Schwartz

[57] ABSTRACT

Various dialkylammonium-2,4-dichlorophenoxyacetates having the formula

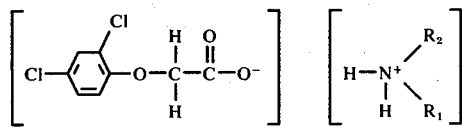

wherein $R_1$ and $R_2$ are radicals each selected from the group consisting of methyl and ethyl, are useful as plant growth regulators. Mono-substituted alkylamines are not suitable for processing into compounds of this invention. The compounds of the invention exhibit excellent water solubility characteristics and possess an exceptionally high and unexpected degree of effectiveness as a general weed killer on lawns, pasture lands, ponds, lakes, canals, ditches, etc. Methods of using and preparing these compounds are disclosed.

28 Claims, 4 Drawing Figures

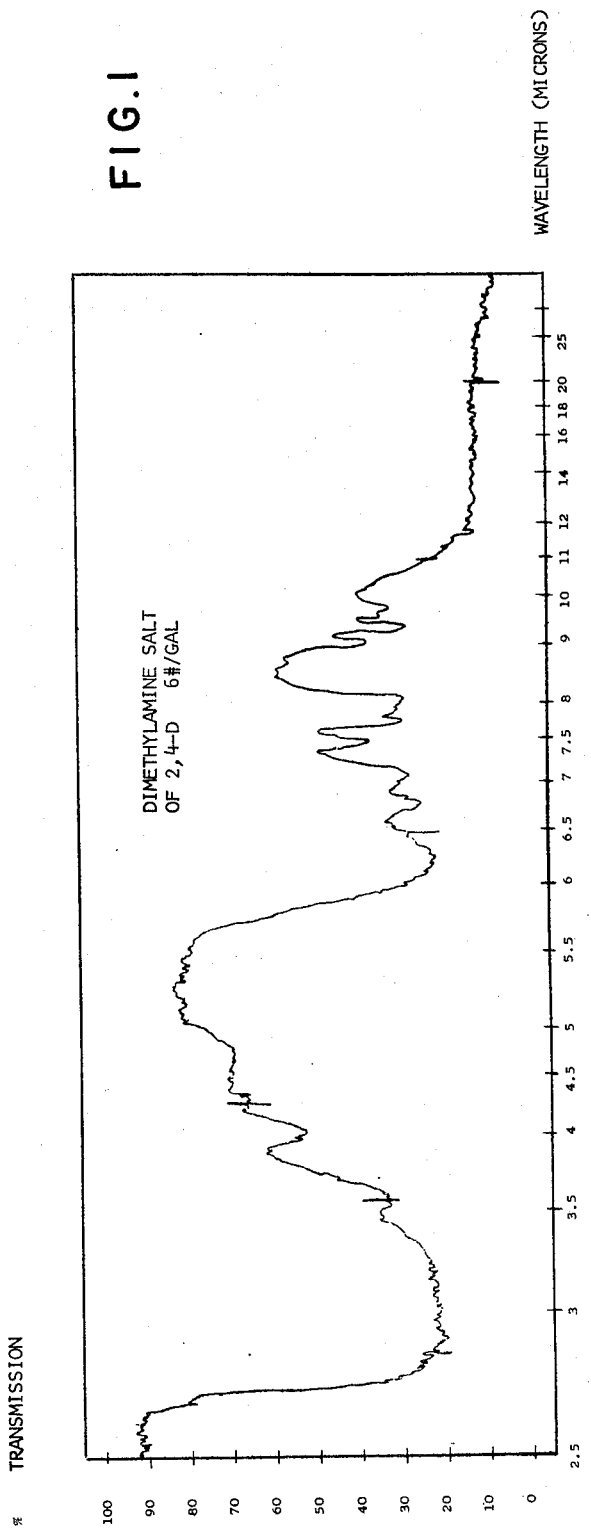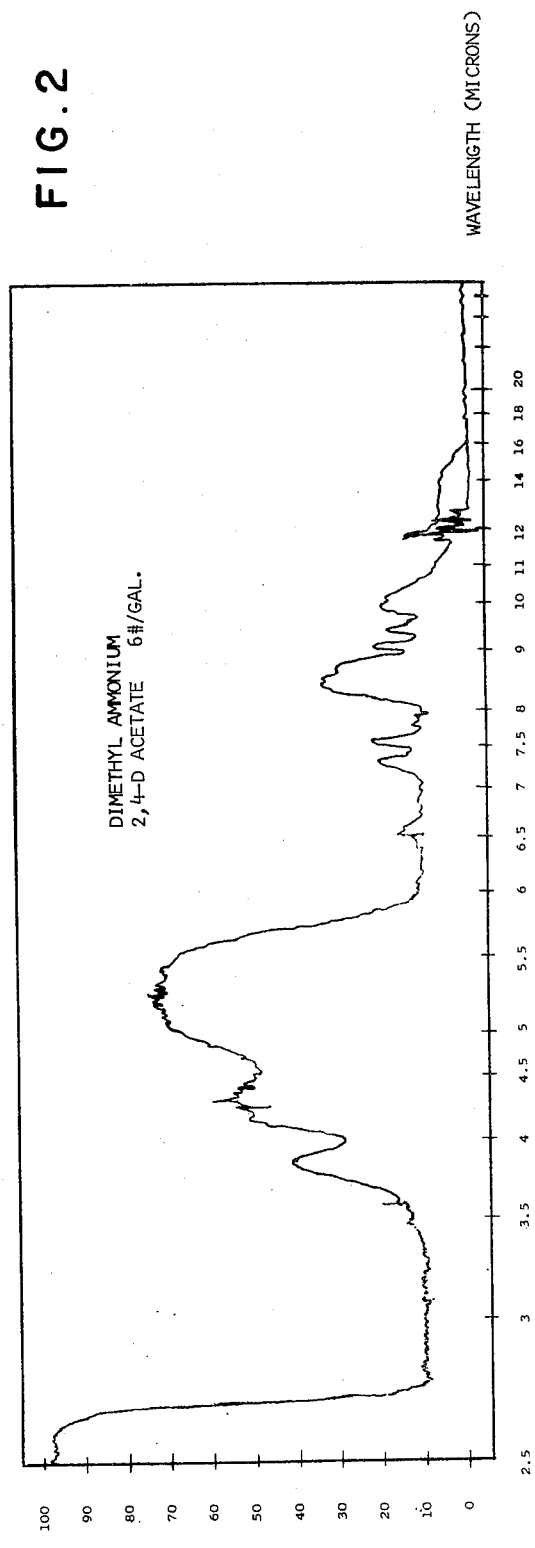

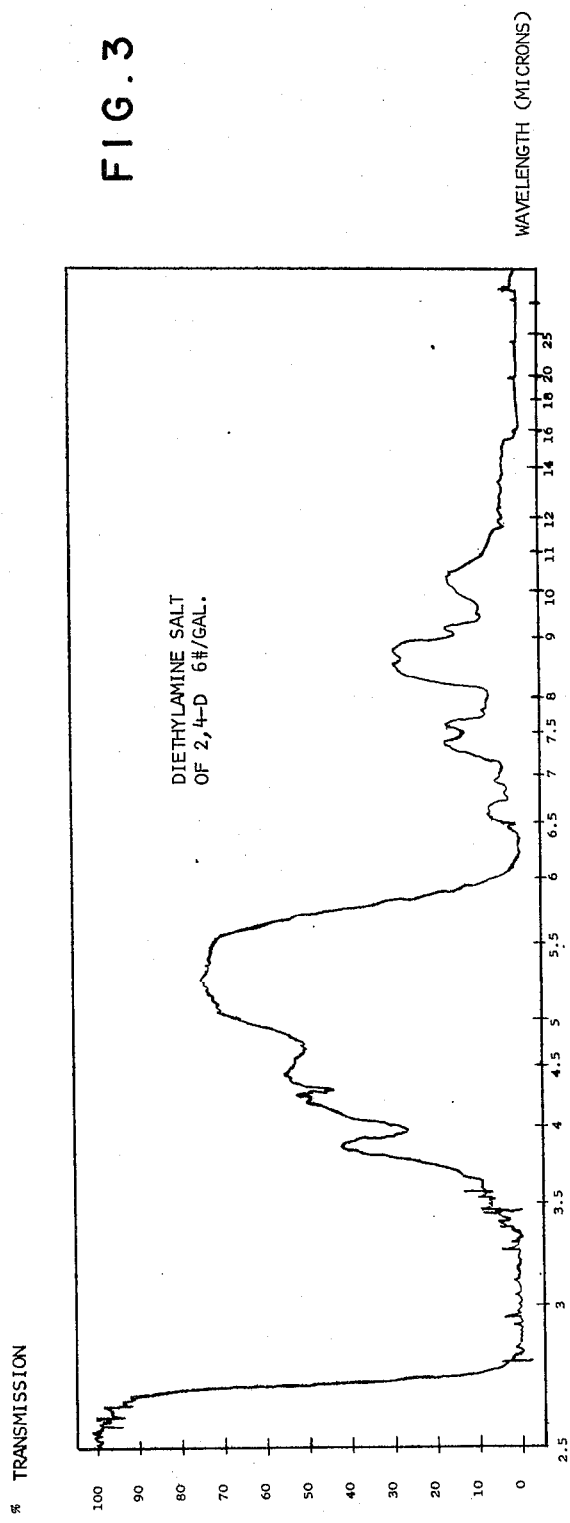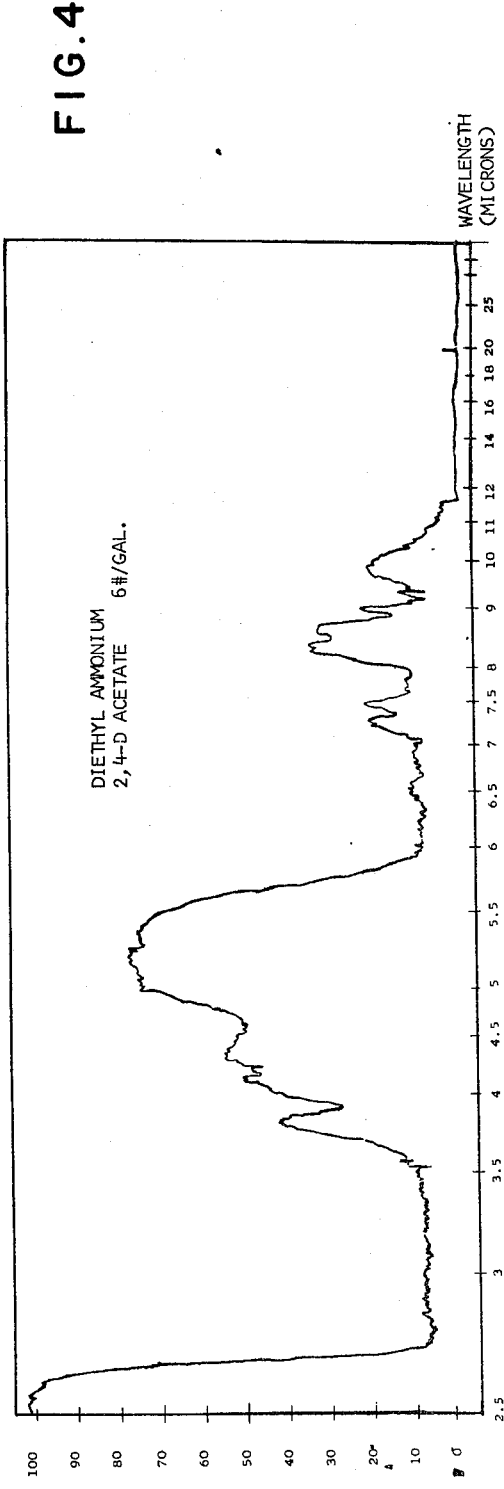

DIALKYLAMMONIUM-2,4-DICHLOROPHENOXYACETATES AS PLANT GROWTH REGULATORS AND THE METHOD OF MAKING SAME

This application is a continuation-in-part application of my copending U.S. patent application Ser. No. 179,333, filed Sept. 10, 1971, now abandoned, which in turn is a continuation-in-part of my U.S. patent application, Ser. No. 33,078, filed Apr. 29, 1970 and now abandoned, which in turn is a continuation-in-part of my U.S. patent application, Ser. No. 4,087, filed Jan. 19, 1970, and now abandoned, which in turn is a continuation-in-part of my U.S. patent application Ser. No. 700,967, filed Jan. 26, 1968, and now abandoned.

BACKGROUND OF THE INVENTION

This invention relates to the production of novel chemical compounds and more particularly to novel dialkylammonium-2,4-dichlorophenoxyacetates having totally unexpected plant growth regulating properties, to compositions containing such compounds, and to methods for utilizing the same for plant growth regulating purposes.

Increasing use has been made of various types of chemicals as plant growth regulators, i.e., for altering the growth characteristics of various types of plants including weeds, which is accomplished by a number of methods. Although various chemicals have been previously proposed for the removal of weeds and otherwise regulating the growth characteristics of plants, these chemicals have not been satisfactory for one or more reasons including their high cost of production, their insufficient or excessive activity, unfavorable rates of disappearance of weeds and chemical, drift problems, adverse effects on grass, rice or marine life, insolubility in water, etc.

OBJECTS OF THE INVENTION

Specifically, it is a primary object of the invention to provide an effective herbicide which is water soluble and which is especially effective for achieving complete control, complete extermination and/or removal of a weed species after it has once infested the area to be protected, at reasonable costs and the herbicide compounds prevent contamination of the environment.

Consistent with this primary object, it is a further object hereof to provide a herbicidal compound which can be made readily available at reasonable prices and which can be incorporated into a variety of agricultural compositions thereby facilitating its application and use.

Still another object of the invention is the provision of a method for employing such novel chemical compounds and compositions to kill weeds, i.e., plants which persist in growing wherein they are not wanted, and preventing the growth of weeds.

Another, most important object of this invention is the provision of novel herbicides which exhibit a remarkably favorable rate of disappearance from soil after application and thus avoid residual action remaining in the soil after the peak desired period for weed control has passed.

A still further object of the invention is to provide a herbicidal compound which is useful as a general weed killer on lawns, golf courses, parks, playgrounds, recreational areas, along highways, railroad right-of-ways, airfields, pasture lands, sod farms, around farm buildings, on ponds, lakes, canals, ditches and streams with effects visible in a few days. These compounds do not have any adverse effects on aquatic life nor on water so treated when used for irrigation, human and animal purposes.

The invention will be better understood and objects other than those set forth above will become apparent after reading the following detailed description of the invention.

DETAILED DESCRIPTION OF THE INVENTION

The attainment of the above objects is made possible by the discovery that improved and unexpected herbicidal activity is possessed by a novel group of dialkylammonium-2,4-dichlorophenoxyacetates having the formula:

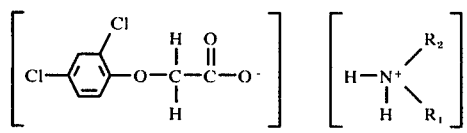

wherein $R_1$ and $R_2$ are radicals each selected from the group consisting of methyl and ethyl.

The dimethylammonium-2,4-dichlorophenoxyacetate exhibits an infra-red absorption according to FIG. 2 which is to be contrasted with the infra-red spectrophotometric examination for the prior art compound dimethylamine salt of 2,4-dichlorophenoxyacetate as illustrated in FIG. 1. Similarly, the infra-red spectrophotometric examination illustrates the difference in absorption characteristics for diethylammonium-2,4-dichlorophenoxyacetate when compared to the prior art compound diethylamine salt of 2,4-dichlorophenoxyacetic acid (see FIGS. 3 and 4).

Particularly preferred herbicidal compounds include dimethylammonium-2,4-dichlorophenoxyacetate and diethylammonium-2,4-dichlorophenoxyacetate.

This novel group of compounds possess totally unexpected herbicidal and plant growth regulating properties when compared to similar compounds known in the prior art as well as when compared to its higher homologues. For example, compounds such as dipropylammonium-2,4-dichlorophenoxyacetate, and those dialkylammonium-2,4-dichlorophenoxyacetates having alkyl groups above ethyl, such as hexyl and butyl, are not water soluble compounds, water solubility being an important property of the novel compounds of the invention. Unlike the compounds of this invention, derivatives of 2,4-dichlorophenoxyacetic acid, a well-known herbicide, and the higher homologues of the compound, must be emulsified to prevent precipitation and to exhibit sufficient herbicidal activity. One of the serious drawbacks in using the emulsified compounds is a reduction in the herbicidal action of the compounds. The water-soluble compounds of this invention, unlike the aforementioned compounds, are able to penetrate the vascular section of plants readily. Being water-soluble, the compounds of this invention also remove themselves from ponds and other water areas by means of adsorption and/or absorption on the mud, silt and non-target weeds.

Thus, the compounds of this invention have been found to be particularly valuable agents for weed control because they are toxic to many sepcies and groups of weeds while they are non-toxic to many beneficial plants.

Weeds are undesirable plants in their growing where they are not wanted, having no economic value, and interfering with the production of cultivated crops or with the welfare of livestock or with the navigation on waterways. Many types of weeds can be controlled by the use of the compounds of the invention and include, for example, alligatorweed, arrowhead beggarweed, bindweed, bitter watercress, box elder, buckhorn, bullthistle, bullrush, burdock, buttercup, Canada thistle, carpetweed, catnip, chickweed, chicory, cocklebur, creeping jenny, cudweed, curly indigo, dichonda, dogfennel, duckweed, elderberry, false dandelion, geranium, goldenrod, hemp, henbit hoary cress, honeysuckle, indigo, ironweed, jimsonweed, lambsquarter, locoweed, morning glory, mullein, mustard, parrot feather, pennywort, pepperweed, pigweed, poison ivy, poisonweed, poorjoe, puncture vine, purslane, ragweed, red sorrel, rush, Russian thistle, sagebrush, shepherds purse, smartweed, sow thistle, Spanish needles, spiny amaranth, stinkweed, sumac, sunflower, thistles, Virginia creeper, waterhyacinths, waterlily, waterlettuce, waterprimrose, wild garlic, wild lettuce, wild onion, wild radish, willow, witchweed.

PREPARATION

The novel dialkylammonium-2,4-dichlorophenoxyacetates of the invention can be prepared by first mixing a dialkylamine having the formula $R_1R_2NH$ wherein $R_1$ and $R_2$ are selected from the group consisting of methyl and ethyl, together with dichlorophenoxyacetic acid or in the presence of an inert solvent, such as an alcohol or water. One mole of 2,4-dichlorophenoxyacetic acid is preferably dissolved in 1.25 moles of the dialkylamine. The product is then dried under reduced heat (i.e., preferably from about 50° C to about 95° C) and reduced pressure resulting in the formation of the desired product. Temperatures at or greater than 100° C result in the formation of a water-insoluble product. Accordingly, extreme care must be exercised to carry out the drying step at temperatures below 100° C. If an alcohol is employed as an inert solvent, it is recovered by distillation and the product taken to dryness under reduced heat and pressure.

According to a preferred embodiment of the invention, dimethylammonium-2,4-dichlorophenoxyacetate is formed by dissolving one mole of 2,4-dichlorophenoxyacetic acid in 1.25 moles of 40% aqueous dimethylamine while maintaining the reaction at 20° C. The product is vacuum dried at 70° C. An elemental analysis of the product provides the following results:

|  | Analysis | Theoretical ($C_{10}H_{13}NO_3Cl_2$) |
|---|---|---|
| Carbon | 45.06% | 45.14% |
| Hydrogen | 4.79% | 4.92% |
| Oxygen | 18.11% | 18.04% |
| Nitrogen | 5.29% | 5.26% |

The product resulting therefrom is crystalline (monoclinic, large crystals), light brown color, molecular weight of 266,11, water soluble, and has a melting point of about 93° C, and preferably from about 92.8 to 93.4° C. This product is unlike the dimethylamine salt of 2,4-dichlorophenoxyacetic acid which is not crystalline and usually exists only in a water solution, but when crystallized, has a melting point of 85° to 87° C.

According to another preferred embodiment of the invention, diethylammonium-2,4-dichlorophenoxyacetate is prepared by dissolving one mole of 2,4-dichlorophenoxyacetic acid in 1.25 moles of 25% aqueous solution of diethylamine. The product is then vacuum dried at 70° C and 4 mm pressure, yielding a light brown, water-soluble crystal having a melting point of 48° C. Herbicidally, the dimethylammonium derivative is more effective than the diethylammonium derivative.

When other higher dialkylamines such as dipropylamine, diisopropylamine, dibutylamine, diisobutylamine and diamylamine were substituted for the various dialkylamines employed in the practice of the invention, the resulting products were found to be water-insoluble and thus did not appear to be suitable for the practice of this invention.

The compounds of the present invention may be applied directly or indirectly to any part of a weed, which is preferably in an active state of growth. Such compounds are soluble in the tissues of the weed, selectively absorbed into the leaves of the weed, and translocated throughout the weed system to the roots to exert their desired herbicial and growth regulating effects. They may be applied either to the growing weeds, weed seedlings or to the soil adjacent thereto or in which the weeds are germinating or expected to germinate. It will be understood that because of the high activity of these compounds, they must generally be employed in relatively small amounts.

In order to establish the fact that there is a difference in chemical structure of the compounds of this invention, namely dimethyl- and diethylammonium-2,4-dichlorophenoxyacetates and the most closely related prior art compounds (the dimethylamine and diethylamine salts of 2,4-dichlorophenoxyacetic acid), comparative infra-red spectrophotometric examinations of each of the aforementioned compounds were conducted. The results of the tests are set forth in FIGS. 1 to 4 of the drawings. By referring to FIGS. 1 and 2, it is apparent that N,N-dimethylammonium-2,4-dichlorophenoxyacetate (FIG. 2) and dimethylamine salt of 2,4-dichlorophenoxyacetic acid (FIG. 1) vary notably in absorption characteristics in the wave length areas of:

3.2 – 4.1 microns
5.75 microns
6.25 – 6.7 microns
7.5 – 8.0 microns
8.0 – 8.2 microns
9.0 – 10.0 microns
10.0 – 13.0 microns There are also minor differences in other areas of the curve.

With reference to FIGS. 3 and 4, it becomes apparent that N,N-diethylammonium-2,4-dichlorophenoxyacetate (FIG. 4) and diethylamine salt of 2,4-dichlorophenoxyacetic acid (FIG. 3) also vary notably in absorption characteristics in the following wave length areas:

3.2 – 3.8 microns
4.2 – 4.7 microns
6.3 – 6.7 microns
7.0 – 7.5 microns
9.0 – 10.0 microns
10.0 – 12.0 microns Minor differences also exist in other areas of the curve.

In carrying out the spectrophotometric examinations discussed above, each of the compounds were prepared with 2,4-dimethylphenoxyacetic acid (99% pure) that was recrystallized from hot alcohol yielding a clean, white to light tan product. This material was dried at a reduced pressure over dessicant.

For the production of the amine salts, two portions, each containing one mole of the acid, were each suspended in distilled water. One mole of dimethylamine and one mole of diethylamine were each added with stirring to each of the aqueous acid mixtures until the solution was complete. Each of the solutions were then diluted to provide an equivalence of six pounds of acid per gallon.

Two one mole samples of the 2,4-dichlorophenoxyacetic acid was suspended in distilled water. An aqueous solution of 1.25 moles of dimethylamine and another aqueous solution of 1.25 moles of diethylamine were each added to the acid solutions, with stirring, until the solution was complete. Each of the two solutions were then evaporated to dryness under vacuum at 5 millimeters absolute pressure at 70° C. Each of the products were then dissolved in distilled water at an equivalence of six pounds of acid per gallon.

COMPOSITIONS

The compositions of the present invention are prepared by admixing at least one compound of the formula

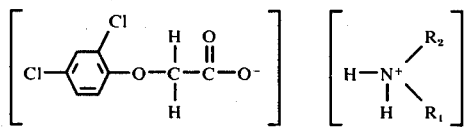

wherein $R_1$ and $R_2$ are radicals each selected from the group consisting of methyl and ethyl. Thus, according to another embodiment of the invention, a herbicidal composition comprising a cogeneric mixture of dialkylammonium-2,4-dichlorophenoxyacetate (e.g., dimethylammonium-2,4-dichlorophenoxyacetate and diethylammonium-2,4-dichlorophenoxyacetate can also be employed. While it is possible to utilize the novel compounds and mixtures thereof alone, a preferred embodiment of the invention includes the use of at least one of said novel compounds in combination with an inert carrier, such as a liquid or a finely divided solid. The inert carrier can be water, alcohol, acetone, or other organic solvents miscible with water, as well as mixtures thereof. The various inert carriers that can be employed in the practice of the inventions are well known to those skilled in the art.

Concentrated solutions of N,N-dimethylammonium-2,4-dichlorophenoxyacetate is stable when stored at temperatures as low as 0° F and have a shelf life of at least 3½ years. In contrast thereto, corresponding solutions of the dimethylamine salt of 2,4-dichlorophenoxyacetic acid are unstable with the basic acid being precipitated within 72 hours.

In the formulation of products for application as an anhydrous application, the described active compounds can be uniformly admixed with any of the well-known free-flowing particulate dry inert solid carriers which may be organic or inorganic such as sawdust, the flour derived from soybean, tobacco, walnut shell, wheat, wood, by-product lignin and lignocellulose, ligninsulfonic acid, cork, urea-formaldehyde and other resins, silicas, carbonates, calcite and dolomite, silicates, clays, tricalcium phosphate, boric acid, etc.

These products should preferably have a particle size of about 25 to 80 mesh screen test, which can be obtained with the usual mixing, blending or grinding equipment and can generally contain, in addition to the inert carrier, about 0.5 to about 50 weight percent of the active compound, and preferably about 30 to about 40 weight percent. In addition, the compositions may optionally contain from about 0.5 to about 1.0 weight percent of a dispersing agent and from about 0.5 to about 1.0 weight percent of a wetting agent, which renders the products wettable and dispersible, thereby facilitating the application thereof in the field, can also be optionally employed. The ingredients can be simply mixed together thoroughly, or the active compounds sprayed directly on an inert carrier with agitation after which the mixture is a free flowing product. Examples of suitable formulations are as follows:

EXAMPLE 1

A composition which is adapted for direct application and useful for the destruction and/or prevention of weeds was prepared. The product is made by blending or mixing the ingredients to give a composition having an average particle size less than 50 microns. The composition includes:

|  | Weight Percent |
| --- | --- |
| Dimethylammonium-2,4-dichlorophenoxyacetate | 20 |
| Talc | 78.75 |
| Silica Gel | 1.00 |
| Methyl Cellulose | 0.25 |

Compositions of the novel active compounds together with the dry inert solid carriers, such as those described hereinbefore, can also be formulated into granules and pellets. In such compositions, the inert solid carrier will generally range from about 50 to about 70 weight percent and the active ingredient can range from about 30 to 50 weight percent. It should be understood that it is not necessary to include a surface active agent in the granular and pelletized compositions.

Pelletized materials are formed by spraying a solution of the dialkylammonium-2,4-dichlorophenoxyacetate upon an inert carrier while the inert carrier is being mixed in a suitable mixer. Thus, according to a preferred embodiment of the invention, 750 pounds of a 25 mesh clay is placed in a 1,000 pound ribbon type dry powder mixer and 250 pounds of dimethylammonium-2,4-dichlorophenoxyacetate that has been melted at 95° C is sprayed on the carrier as the carrier is being mixed. The dimethylammonium-2,4dichlorophenoxyacetate sets on the surface of the clay, resulting in the formation of a free flowing material that disintegrates slowly when it comes into contact with moisture. Fertilizers can replace the clay. Similar types of granular compositions are set forth in Examples 2 and 3. These compositions can be used in its present state or mixed with water to form a paste and then extruding the paste and drying the paste under reduced heat and pressure to provide a granular product which is preferably in the order of one thirty-second to one quarter inch in diameter.

EXAMPLE 2

Two parts by weight of crystalline N,N-dimethylammonium-2,4-dichlorophenoxyacetate is heated at 95° C to form a matted product. Three parts by weight of diatomacious clay is mixed with the melt and stirred. The mixture is then permitted to cool to form a crystalline material, said material being ground to form a pulverized product wherein the particles are of about 80 mesh.

EXAMPLE 3

Two parts by weight of crystalline N,N-dimethylammonium-2,4-dichlorophenoxyacetate are heated at 95° C to form a melted product. Three parts by weight of 80 mesh diatomacious clay, heated to 100° C is then mixed with the melted product for about 30 minutes. The mixture is then permitted to cool, forming a crystalline product, said product then being ground to form a pulverized product capable of passing through an 80 mesh screen. A surface active agent may be added in an amount of up to 1% by weight of said composition.

EXAMPLE 4

A composition was formed, which, when added to water, resulted in the control of plant growth:

|  | Weight percent |
| --- | --- |
| Dimethylammonium-2,4-dichlorophenoxyacetate | 40.0 |
| 80 mesh diatomacious clay | 60.0 |

The surface-active agent useful in the practice of the invention can include such anionic, cationic and non-ionic agents as have heretofore been generally employed in similar herbicidal and plant growth regulating compositions. Suitable surface-active agents are set forth, for example, in Searle, U.S. Pat. No. 2,426,417; Todd, U.S. Pat. No. 2,655,447; Jones, U.S. Pat. No. 2,412,510; or Lehner, U.S. Pat. No. 2,139,276. A detailed list of such agents is also set forth in "Detergents and Emulsifiers Annual" (1964) by John W. McCutcheon, Inc.

Suitable surface-active agents useful as dispersing and/or wetting agents in compositions of the present invention include: polyethylene glycol fatty acid esters and fatty alkylol amide condensates, alkylaryl sulfonates, fatty alcohol sulfates, dialkylesters of sodium isothionate, polyoxyethylene ethers and thioethers and long chain quaternary ammonium chloride compounds.

Surface active dispersing agents such as sodium lignin sulfonates, low viscosity methyl cellulose, polymerized sodium salts of alkyl naphthalene sulfonic acids are also suitable in the hebicidal and plant growth regulating compositions of the invention.

Among the more preferred surfactants are the anionic and non-ionic type. Among the anionic surface-active agents, preferred ones are alkali metal or amine salts of alkylbenzene sulfonic acids such as dodecyl benzene sulfonic acid, sodium lauryl sulfate, alkylnaphthalene sulfonates, oleic acid ester of sodium isothionate, dioctyl sodium sulfonsuccinate, etc. Among the non-ionic compounds, preferred members are alkylphenoxy poly(ethyleneoxy) ethanols such as nonylphenol adducts with ethylene oxides; trimethylnonyl polyethylene glycol ethers, polyethylene oxide adducts of fatty rosin acids, long chain alkyl mercaptans adducts with ethylene oxide.

In general, less than 2 weight percent of the surface active agents will be used in compositions of this invention and ordinarily the amount of surface active agents will range from 0.5 to 1.0 weight percent.

As pointed out above, the inert carrier may also be a liquid, if, for example, the active compound is to be applied in the form of a spray. The liquid formulations may contain at least 0.5 weight percent of the active compound and preferably from about 0.5 to about 70 weight percent, with actual amounts being determined by several factors such as the nature of the liquid diluent, the intended use, and the like.

In producing the liquid formulations containing the active compound, at least one of the active compounds can be admixed with at least one of the following inert solvents: water, acetone, alkaline solutions such as aqueous sodium, potassium and ammonium solutions, alcohol and solutions of water-soluble dialkylamines. The active compounds of the invention can also be admixed with various petroleum factions including kerosene, aliphatic hydrocarbons, alkylated naphthalenes, and other mineral lubricating oils where emulsions are desired. These liquid formulations can also include various dispersing and/or wetting agents such as those disclosed herein. Typical alcohols useful in the practice of the invention include those alcohols disclosed in my U.S. Pat. No. 2,900,293, which is hereby incorporated by reference.

The novel herbicidal and plant growth regulating compounds can also be formulated with various types of fertilizer compositions. The fertilizers or plant nutrients, as they are commonly called, include the commonly used compounds of nitrogen, phosphorus, and potassium; i.e., ammonium sulfate, ammonium nitrate, urea, methylene ureas, low molecular weight ureaformaldehyde polymers, sodium nitrate, anhydrous ammonia, aqueous ammoniacal solutions of urea, or ammonium nitrate, ammonium phosphates, superphosphates, triple superphosphates and the phosphoric acid and the potassium salts, such as the chloride, sulfate and nitrate. The plant nutrients are applied individually or in admixture with each other.

The novel dialkylammonium-2,4-dichlorophenoxyacetates are preferably added to such fertilizer mixtures or compounds following the usual mixing, granulation, ammoniation, drying or other manufacturing operations to avoid possible adverse effects of such operations on the compounds when employed as weed retardants.

According to a preferred embodiment of this invention, the dialkylammonium-2,4-dichlorophenoxyacetates are formulated with at least one penetrating agent selected from the group consisting of dimethyl sulfoxide, ethylenediamine tetracetic acid, water-soluble dialkyl disulfide and mixtures thereof. The penetrating agents have been found to be particularly valuable agents for assisting the herbicidal agents in penetrating the vascular section of the plants being treated. In general, the herbicidal compositions containing about from 5 to 25 weight percent and preferably 10 percent by weight of the total composition.

The following examples illustrate typical compositions utilizing the above penetrating agents:

EXAMPLE 5

| | Weight percent |
|---|---|
| Dimethylammonium-2,4-dichlorophenoxyacetate | 67 |
| Dimethyl Sulfoxide | 10 |
| Ethylenediamine tetracetic acid (chelating agent) | 10 |
| Water | 13 |

One quart of this solution in 50 gallons of water controls thistle on an acre surface so efficiently that there is no regrowth the following year. Water-soluble dialkyl disulfides can be substituted for the dimethyl sulfoxide in this example. It is also understood that other chelating agents may be used in this or other compositions of this invention.

EXAMPLE 6

| | Weight percent |
|---|---|
| Dimethylammonium-2,4-dichlorophenoxyacetate | 65 |
| Ethylenediamine tetraacetic acid | 10 |
| Water | 25 |

One quart of this solution in 50 gallons of water and sprayed on an acre of fairway controlled all broad leaf weeds with no damage to grass.

EXAMPLE 7

| | Weight percent |
|---|---|
| Dimethylammonium-2,4-dichlorophenoxyacetate | 67 |
| Dimethyl Sulfoxide | 10 |
| Ethylenediamine tetraacetic acid | 10 |
| Alkylated aryl polyether alcohol | 3 |
| Water | 10 |

One quart of this solution in 50 gallons of water applied to one acre of sugar cane controls all broad leaf weeds, purslane and matured pigweed.

It will be understood that the herbicide compounds of the present invention may be applied in 100 percent form, but this is impractical because of difficulties in handling, measuring, applying, etc. Formulated compositions as described above are therefore preferred. Regardless of whether the active compound is applied pure or in formulations to the plant or weed to be treated, or its environs, it is always used in an effective or herbicidal amount, which amount is readily ascertainable by a person of ordinary skill in the art by routine experimentation. It will be understood that these compositions may contain other functional agents and assistants such as pesticides, including insecticides, arachnicides, bactericides, fungicides, and the like, as well as other herbicides, bonding, spreading, and sticking agents.

Other useful herbicidal compositions according to this invention are illustrated in the following examples:

EXAMPLE 8

| Liquid Formulation | Weight percent |
|---|---|
| Dimethylammonium-2,4-dichlorophenoxyacetate | 50 |
| 3,9-diethyltridecanol-6-sodium sulfate (wetting agent) | 1 |
| Water | 48.75 |
| Methyl cellulose, 1500 cps (dispersing agent) | 0.25 |
| | 100.00 |

EXAMPLE 9

| Liquid Formulation | Weight percent |
|---|---|
| Dimethylammonium-2,4-dichlorophenoxyacetate | 50 |
| 3,9-diethyltridecanol-6-sodium sulfate (wetting agent) | 1 |
| Water | 48.75 |
| Methyl Cellulose, 1500 cps (dispersing agent) | 0.25 |
| | 100.00 |

APPLICATION

Bodies of water such as drainage ditches, lakes, ponds, canals, rivers, reservoirs, and the like, can be treated with the present herbicidal compounds or compositions containing the same as described above to control undesirable aquatic vegetation including floating, partially submerged, and totally submerged weeds. In these aquatic applications, the present compounds and compositions may be applied upon or below the surface of the water in effective amounts sufficient to control the desired weed.

Effective amounts for aquatic vegetation floating and partially submerged are from about 3 to 6 pounds of the active herbicide compound per acre. For submerged aquatic vegetation, from about 20 to about 50 pounds per acre, the latter amount being dependent on the density of the underwater aquatic vegetation.

Application of the herbicidal and plant growth regulator compounds and compositions is preferably made to the soil at or before the time of planting or between planting and the emergence of desirable plants. The exact amount of compound required will depend on a variety of factors including the hardiness of the particular weed species, weather, method of application, the kind of beneficial plant seeds in the same area, and the like. Thus, while the application of one or two ounces of the active compound per acre may be sufficient for good control of a light infestation of weeds, the application of three pounds or more of active compound per acre may be required for good control of a dense infestation of weed under favorable conditions.

Tests conducted by the U.S. Department of Agriculture show dimethylammonium-2,4-dichlorophenoxyacetate is four times more effective for the control of alligatorweed than the dimethylamine salt of 2,4-dichlorophenoxyacetic acid.

Tests conducted by the Game and Fresh Water Fish Commission, State of Florida, show that dimethylammonium-2,4-dichlorophenoxyacetate at six pounds of active ingredient in 100 gallons of water, applied to one acre of water surface, has no ill effects on the breathing or spawning of fish.

Tests conducted by the United States Fish and Wildlife Service, U.S. Department of the Interior, show that fish do not assimilate dimethylammonium-2,4-dichlorophenoxyacetate at six pounds of active ingredient to 100 gallons of water when metered into a test tank for two weeks. Further tests by the Game and Fresh Water Fish Commission of the State of Florida show this compound has no ill effect on aquatic life. In view of these and other extensive tests conducted on the compounds of this invention, the United States Environmental Protection Agency has granted approval for the use of N,N-dimethylammonium 2,4-dichlorophenoxyacetate in the environment.

Having now discussed in considerable detail illustrative and preferred embodiments of the invention, it should be apparent that the objects set forth at the outset of this specification have been satisfied. Accordingly,

What is claimed is:

1. A compound of the formula

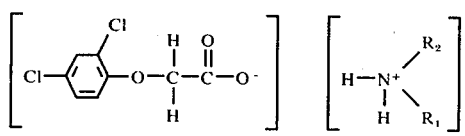

wherein $R_1$ and $R_2$ are identical radicals selected from the group consisting of methyl and ethyl, (a) when said $R_1$ and $R_2$ are both methyl, said compound has an infrared spectra according to FIG. 2 and a melting point from about 92.8° to 93.4° C., and (b) when said $R_1$ and $R_2$ are both ethyl, said compound has an infra-red spectra according to FIG. 4 and a melting point of about 48° C.

2. The compound according to claim 1, which is dimethylammonium-2,4-dichlorophenoxyacetate.

3. The compound according to claim 1, which is diethylammonium-2,4-dichlorophenoxyacetate.

4. A herbicidal composition comprising at least one of said compounds defined in claim 1, said compound being present in a herbicidal amount.

5. A herbicidal composition comprising an inert carrier and as an essential active ingredient, a compound according to claim 1 said compound being present in a herbicidal amount.

6. A herbicidal composition comprising an inert carrier and as an essential active ingredient, a compound according to claim 3.

7. A herbicidal composition comprising an inert carrier and as an essential active ingredient, a compound according to claim 2.

8. A herbicidal composition according to claim 3, wherein said inert carrier is water.

9. A herbicidal composition according to claim 5, wherein said essential active ingredient is dimethylammonium-2,4-dichlorophenoxyacetate and said inert carrier is water.

10. A herbicidal composition according to claim 9, comprising from about 30 to about 70 weight percent of said essential active ingredient and from about 70 to about 30 weight percent of water.

11. A herbicidal composition according to claim 10, further comprising as an additional ingredient thereof, an additive selected from the group consisting of a dispersing agent, wetting agent, and mixtures thereof.

12. A herbicidal composition according to claim 10, comprising 70 weight percent of said essential active ingredient and 30 weight percent water.

13. A herbicidal composition according to claim 11 comprising about 50 weight percent dimethylammonium-2,4-dichlorophenoxyacetate, about 1 weight percent 3,9-diethyltridecanol-6-sodium sulfate, about 0.25 weight percent methyl cellulose (1500 cps) and about 48.75 weight percent water.

14. A herbicidal composition according to claim 5, wherein said inert carrier is a dry inert solid carrier.

15. A herbicidal composition according to claim 14, comprising from about 0.5 to about 50 weight percent of the essential active ingredient.

16. A herbicidal composition according to claim 15, further comprising as additional ingredients thereof, from about 0.5 to 1.0 weight percent of a dispersing agent and from about 0.5 to about 1.0 weight percent of a wetting agent.

17. A herbicidal composition according to claim 16, comprising 20 weight percent of dimethylammonium-2,4-dichlorophenoxyacetate, 78.75 weight percent talc, 1.0 weight percent of silica gel and 0.25 methyl cellulose.

18. A herbicidal composition according to claim 14, comprising about 99.5 weight percent dimethylammonium-2,4-dichlorophenoxyacetate and about 0.5 weight percent of a dispersing agent.

19. A herbicidal composition according to claim 4, comprising a cogeneric mixture of dimethylammonium-2,4-dichlorophenoxyacetate and diethylammonium-2,4-dichlorophenoxyacetate.

20. A herbicidal composition according to claim 5, which further comprises a penetrating agent selected from the group consisting of dimethyl sulfoxide, chelating agents, water-soluble dialkyl disulfides and mixtures thereof.

21. A herbicidal composition according to claim 20 comprising 67 weight percent dimethylammonium-2,4-dichlorophenoxyacetate, 10 weight percent dimethyl sulfoxide, 10 weight percent ethylenediamine tetraacetic acid and 13 weight percent water.

22. A herbicidal composition according to claim 20, comprising 65 weight percent dimethylammonium-2,4-dichlorophenoxyacetate, 10 weight percent ethylenediamine tetraacetic acid and 25 weight percent water.

23. Method for the control of weeds comprising applying to a locus to be protected in an amount sufficient to exert herbicidal action, a compound according to claim 1.

24. Method for the control of weeds comprising applying to a locus to be protected in an amount sufficient to exert herbicidal action, a compound according to claim 2.

25. Method for the control of weeds comprising applying to a locus to be protected in an amount sufficient to exert herbicidal action, a compound according to claim 3.

26. Method for the control of weeds which comprises contacting said weeds with a compound according to claim 1, in an amount sufficient to exert herbicidal action.

27. Method for the control of weeds which comprises contacting said weeds with a compound according to claim 2, in an amount sufficient to exert herbicidal action.

28. Method for regulating the growth of herbs which comprises the step of applying a compound according to claim 1 to a herb in an amount sufficient to regulate the growth of said herb.

* * * * *